(12) United States Patent
Kawai et al.

(10) Patent No.: US 8,016,418 B2
(45) Date of Patent: Sep. 13, 2011

(54) EYE AXIAL LENGTH MEASUREMENT APPARATUS

(75) Inventors: Noriji Kawai, Gamagori (JP); Tetsuyuki Miwa, Nukata-gun (JP); Kunihiko Otake, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 387 days.

(21) Appl. No.: 12/000,756

(22) Filed: Dec. 17, 2007

(65) Prior Publication Data

US 2008/0151188 A1 Jun. 26, 2008

(30) Foreign Application Priority Data

Dec. 26, 2006 (JP) .................. 2006-350681

(51) Int. Cl.
*A61B 3/10* (2006.01)
*A61B 3/14* (2006.01)
(52) U.S. Cl. ....................... 351/205; 351/206
(58) Field of Classification Search .......... 351/204–206, 351/200, 208, 211, 220, 221
See application file for complete search history.

(56) References Cited

U.S. PATENT DOCUMENTS

| | | | |
|---|---|---|---|
| 5,325,135 A | 6/1994 | Nakamura et al. | |
| 5,329,321 A * | 7/1994 | Koizumi | 351/205 |
| 5,463,430 A | 10/1995 | Isogai et al. | |
| 6,779,891 B1 | 8/2004 | Barth et al. | |
| 6,805,442 B2 | 10/2004 | Torii et al. | |
| 7,527,378 B2 * | 5/2009 | Fukuma et al. | 351/205 |
| 2007/0002277 A1 | 1/2007 | Hanebuchi | |

FOREIGN PATENT DOCUMENTS

| | | |
|---|---|---|
| EP | 0 956 810 A1 | 11/1999 |
| EP | 1 602 320 A1 | 12/2005 |
| JP | A 2001-187022 | 7/2001 |
| JP | A 2005-342204 | 12/2005 |
| JP | A 2007-37984 | 2/2007 |

* cited by examiner

*Primary Examiner* — Ricky Mack
*Assistant Examiner* — Tuyen Q Tra
(74) *Attorney, Agent, or Firm* — Oliff & Berridge, PLC (57) ABSTRACT

An eye axial length measurement apparatus includes a light source, a non-contact eye axial length measurement unit for optically measuring axial length of a patient's eye in non-contact manner, an XYZ driving unit, and a determination means which determines whether a cloudy portion which is an obstacle to measurement by the non-contact eye axial length measurement unit is present, based on one of a measurement result of the non-contact eye axial length measurement unit and an imaging result of an anterior segment section imaging unit placeable in the non-contact eye axial length measurement unit.

17 Claims, 7 Drawing Sheets

EYE AXIAL LENGTH MEASUREMENT APPARATUS

BACKGROUND OF THE INVENTION

1. Field of the Invention

The present invention relates to an eye axial length measurement apparatus for measuring an axial length of an examinee's eye (a patient's eye).

2. Description of Related Art

There is known an ultrasonic eye axial length measurement apparatus for measuring an axial length of a patient's eye by making an ultrasonic prove touch a cornea of the patient's eye (see JP2001-187022A for example). Another known one is a non-contact eye axial length measurement apparatus including a measurement optical system arranged to project measuring light to a patient's eye and detect reflection light therefrom and optically measure an axial length of a patient's eye by using an optical interference technique without touching the eye.

A concrete configuration of the non-contact eye axial length measurement apparatus is briefly explained. The measurement optical system includes: an irradiation optical system for splitting light emitted from a low coherent light source to irradiate a cornea and a fundus of a patient's eye; a photo-receiving optical system with a photo-receiving element for photo-receiving interference light generated by reference light and measurement light, one of which is corneal reflection light or fundus reflection light produced by the irradiation optical system and the other is the remainder of them; and an optical path length changing member disposed to be movable into an optical path of the irradiation optical system or the photo-receiving optical system to change an optical path length. Generally, the axial length of the patient's eye is determined based on the moved position of the optical path length changing member when an interference signal is detected by the photo-receiving element (for example, EP1602320A1 (JP 2005-342204A) and US2007/0002277A1 (JP 2007-37984A)). As a system of the measurement optical system, there are known for example a time domain system disclosed in EP '320 and a Fourier domain system disclosed in US '277.

The ultrasonic eye axial length measurement apparatus has an advantage that can measure even a cataract eye. However, eye-drop anesthesia to the patient's eye is required. This is a large burden on a patient and also an additional work for an examiner. On the other hand, the non-contact eye axial length measurement apparatus has an advantage that can perform measurement in non-contact manner without placing a burden on the patient. However, such optical measurement is unsuitable for some patients' eyes. For example, in the case of an eye with severe cataract, measuring light is apt to be blocked by a cloudy portion and it is hard to obtain a high reliable measurement value.

BRIEF SUMMARY OF THE INVENTION

The present invention has been made in view of the above circumstances and has an object to provide an eye axial length measurement apparatus capable of effectively performing eye axial length measurement according to a condition of a patient's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an eye axial length measurement apparatus comprising: a light source which emits low coherent light; a non-contact eye axial length measurement unit for optically measuring axial length of a patient's eye in non-contact manner in such a way that low coherent light emitted from the light source is split into measuring light and reference light, the measuring light and the reference light are caused to interfere with each other, and the eye axial length is calculated based on a difference in optical path length between the measuring light and the reference light when an interference signal is generated; an ultrasonic eye axial length measurement unit including an ultrasonic probe with a transducer, the unit being placed in a position with a deviation from the non-contact eye axial length measurement unit; an XYZ driving unit including a base, a head support unit attached to the base, and a movable unit which supports the non-contact eye axial length measurement unit and ultrasonic eye axial length measurement unit movably in an X-Y-Z directions with respect to the base; and a determination means which determines whether or not a cloudy portion which is an obstacle to measurement by the non-contact eye axial length measurement unit is present, based on one of a measurement result of the non-contact eye axial length measurement unit and an imaging result of an anterior segment section imaging unit placeable in the non-contact eye axial length measurement unit.

According to another aspect, the present invention provides an eye axial length measurement apparatus comprising: a light source which emits low coherent light; a non-contact eye axial length measurement unit for optically measuring axial length of a patient's eye in non-contact manner in such a way that low coherent light emitted from the light source is split into measuring light and reference light, the measuring light and the reference light are caused to interfere with each other, and the eye axial length is calculated based on a difference in optical path length between the measuring light and the reference light when an interference signal is generated; an ultrasonic eye axial length measurement unit including an ultrasonic probe with a transducer, the unit being placed in a position with a deviation from the non-contact eye axial length measurement unit; an XYZ driving unit including a base, a head support unit attached to the base, and a movable unit which supports the non-contact eye axial length measurement unit and ultrasonic eye axial length measurement unit movably in an X-Y-Z directions with respect to the base; and control means for driving the XYZ driving unit in a vertical direction and a horizontal direction, based on a signal representing switching from a measurement mode using the non-contact eye axial length measurement unit to a measurement mode using the ultrasonic eye axial length measurement unit, so that a measurement central axis of the ultrasonic eye axial length measurement unit is adjusted to a position in which a measurement central axis of the non-contact eye axial length measurement unit has been positioned before the switching.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1A:
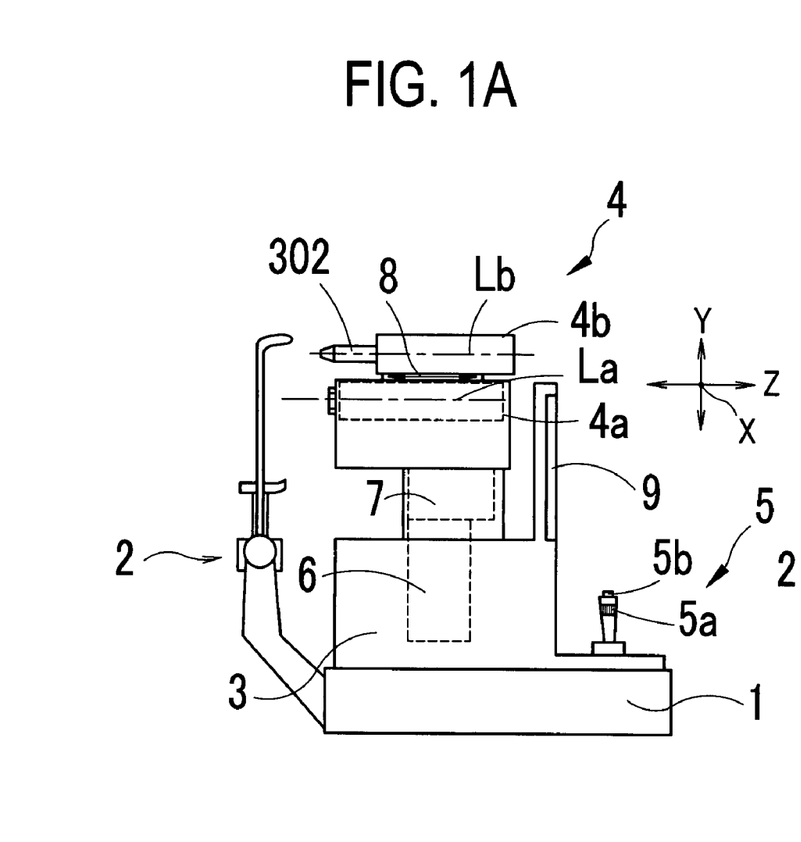
FIGS. 1A and 1B are external views of an eye axial length measurement apparatus of a preferred embodiment.
Figure 1B:
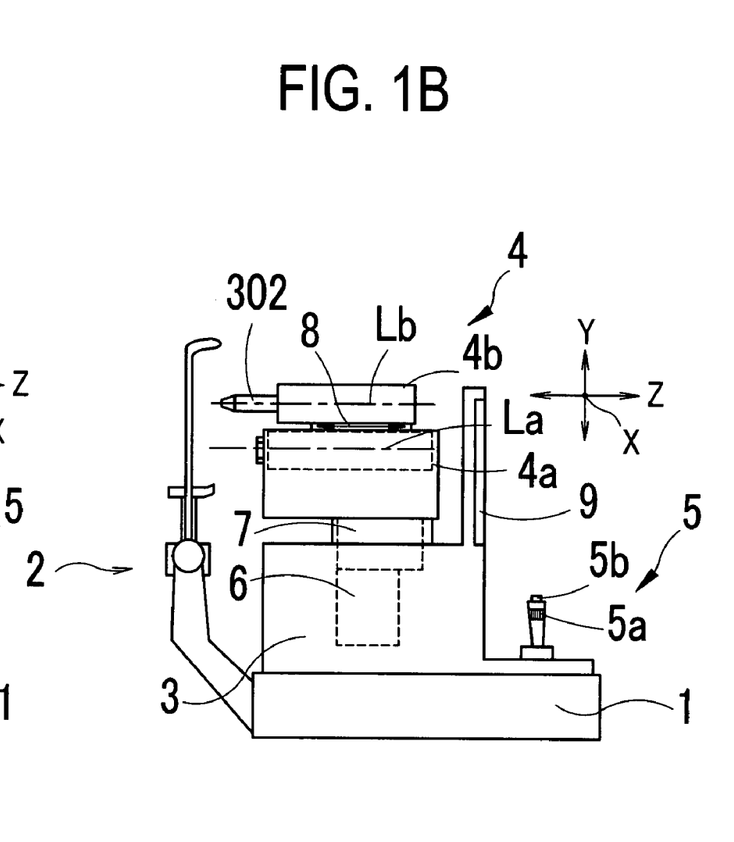

A detailed description of a preferred embodiment of the present invention will now be given referring to the accompanying drawings. FIGS. 1A and 1B are external views of an eye axial length measurement apparatus of the present embodiment.

This eye axial length measurement apparatus includes a table 1, a head support unit 2 attached to the table 1, a movable base 3 mounted on the table 1 to be movable by a sliding mechanism (not shown), and a measurement unit 4 movably mounted on the movable base 3. The measurement unit 4 includes a non-contact eye axial length measurement section 4a (hereinafter, referred to as a "non-contact measurement section 4a") for optically measuring an axial length of a patient's eye and an ultrasonic eye axial length measurement section 4b (hereinafter, referred to as a "contact measurement section 4b") placed on the non-contact measurement section 4a and arranged to measure the eye axial length by touching a distal end of an ultrasonic probe 302 to a cornea of the patient's eye. The apparatus has a non-contact measurement mode for measurement using the non-contact measurement section 4a (see FIG. 1A) and a contact measurement mode for measurement using the contact measurement section 4b (see FIG. 1B). These measurement modes can be switched automatically or manually.

The measurement unit 4 is movable in an up/down direction (Y-direction in FIGS. 1A and 1B) relative to the patient's eye by a Y driving section 6 provided in the movable base 3. The Y driving section 6 is arranged to move the measurement unit 4 in the Y-direction relative to the patient's eye in response to switching between the non-contact measurement mode and the contact measurement mode so that either one of a measuring light axis La of the non-contact measurement section 4a and a measurement axis Lb of the contact measurement section 4b (the distal end of the ultrasonic probe 302) is adjusted to almost the same height of a patient's eye E to be examined, fixedly supported by the head support unit 2.

The measurement unit 4 is also movable in a right/left direction (X-direction) and a back/forth (working distance) direction (Z-direction) with respect to the patient's eye E by an XZ driving section 7 provided on the Y driving section 6.

Accordingly, the measurement unit 4 can be moved in three-dimensional directions. The contact measurement section 4b is placed to be movable in the Z-direction relative to the non-contact measurement section 4a by driving of a driving section 8. In the contact measurement mode, the contact measurement section 4b is moved forward, coming close to the patient's eye E. In the non-contact measurement mode, on the other hand, the contact measurement section 4b is moved backward, separating from the patient's eye E.

The movable base 3 is movable on the table 1 in the X-direction and the Z-direction respectively by operation of a joystick 5. When an examiner turns a rotary knob 5a, the measurement unit 4 is moved in the Y-direction by driving of the Y driving section 6. The joystick 5 is provided with a measurement start button 5b at the top. The movable base 3 is provided with a display monitor 9.

Figure 2A:
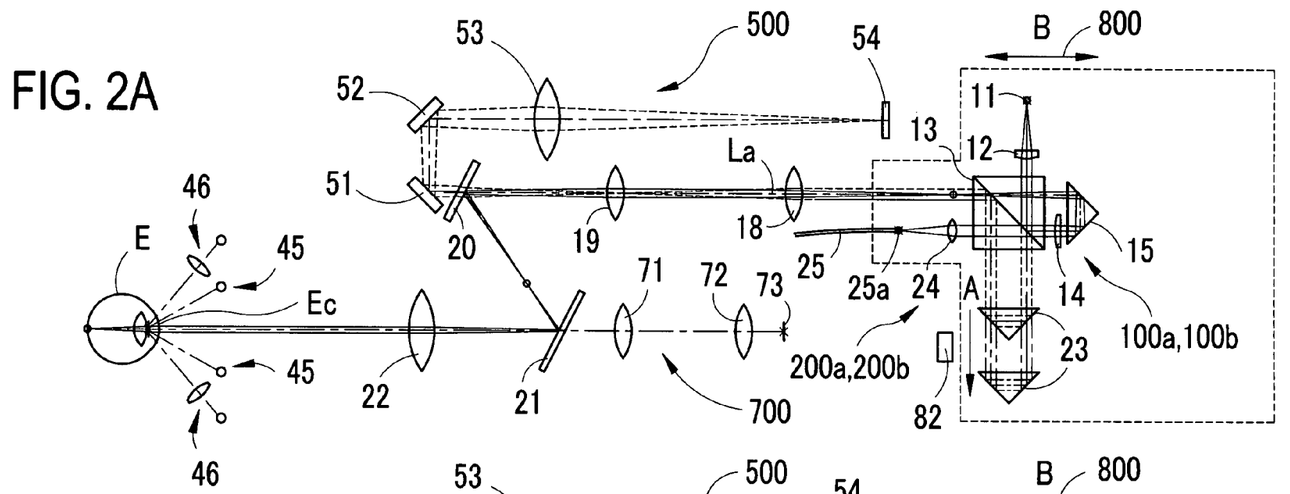
FIGS. 2A and 2B are views for explaining optical systems of a non-contact measurement section.
Figure 2B:
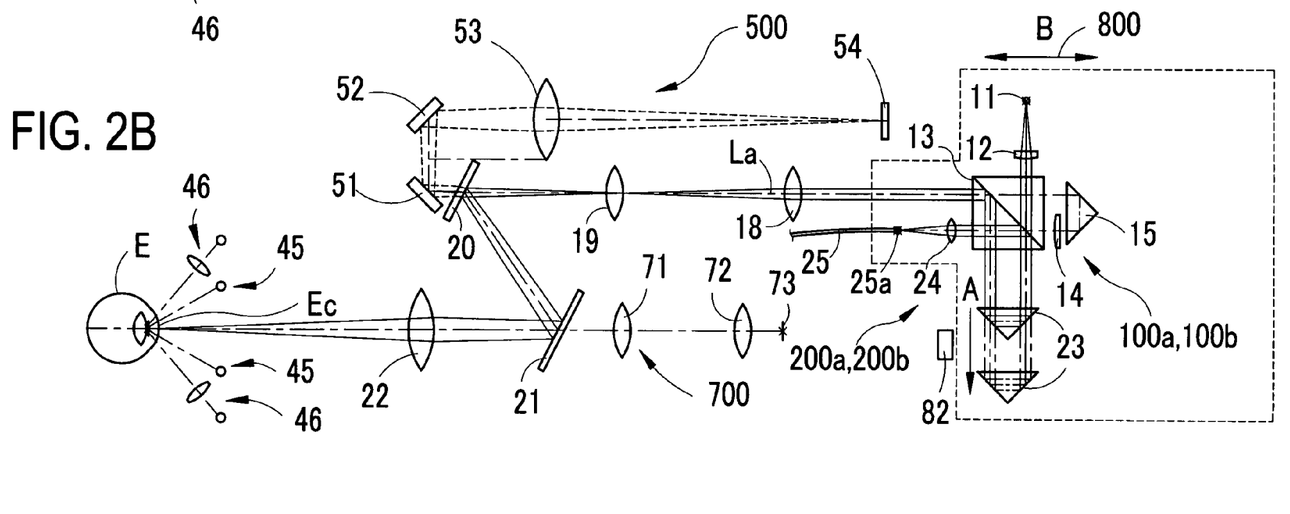
Figure 3:
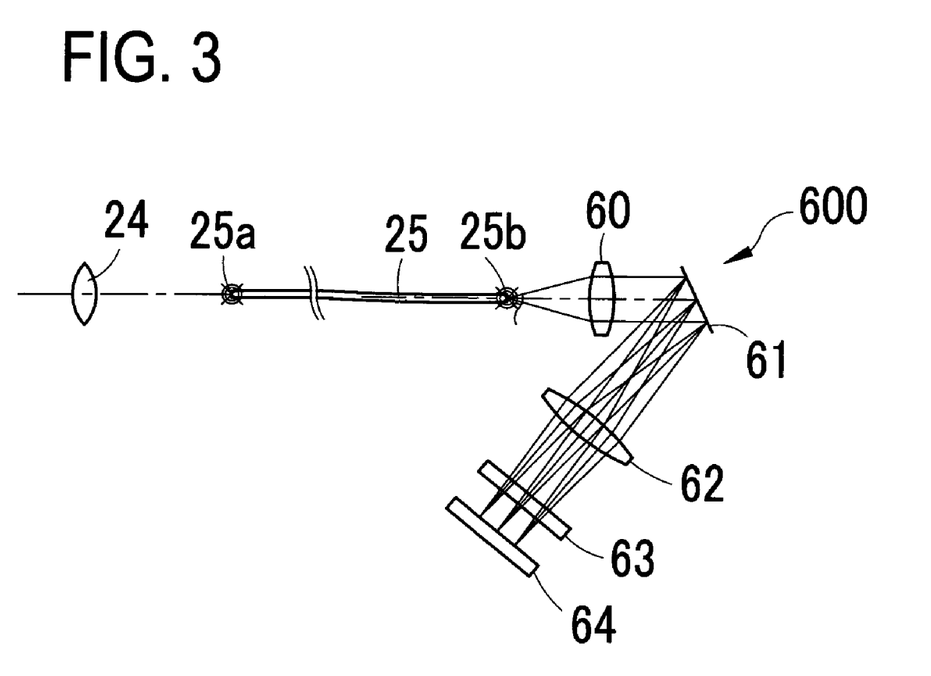
FIG. 3 is a view for explaining a spectral optical system of the non-contact measurement section of the embodiment.
Figure 4:
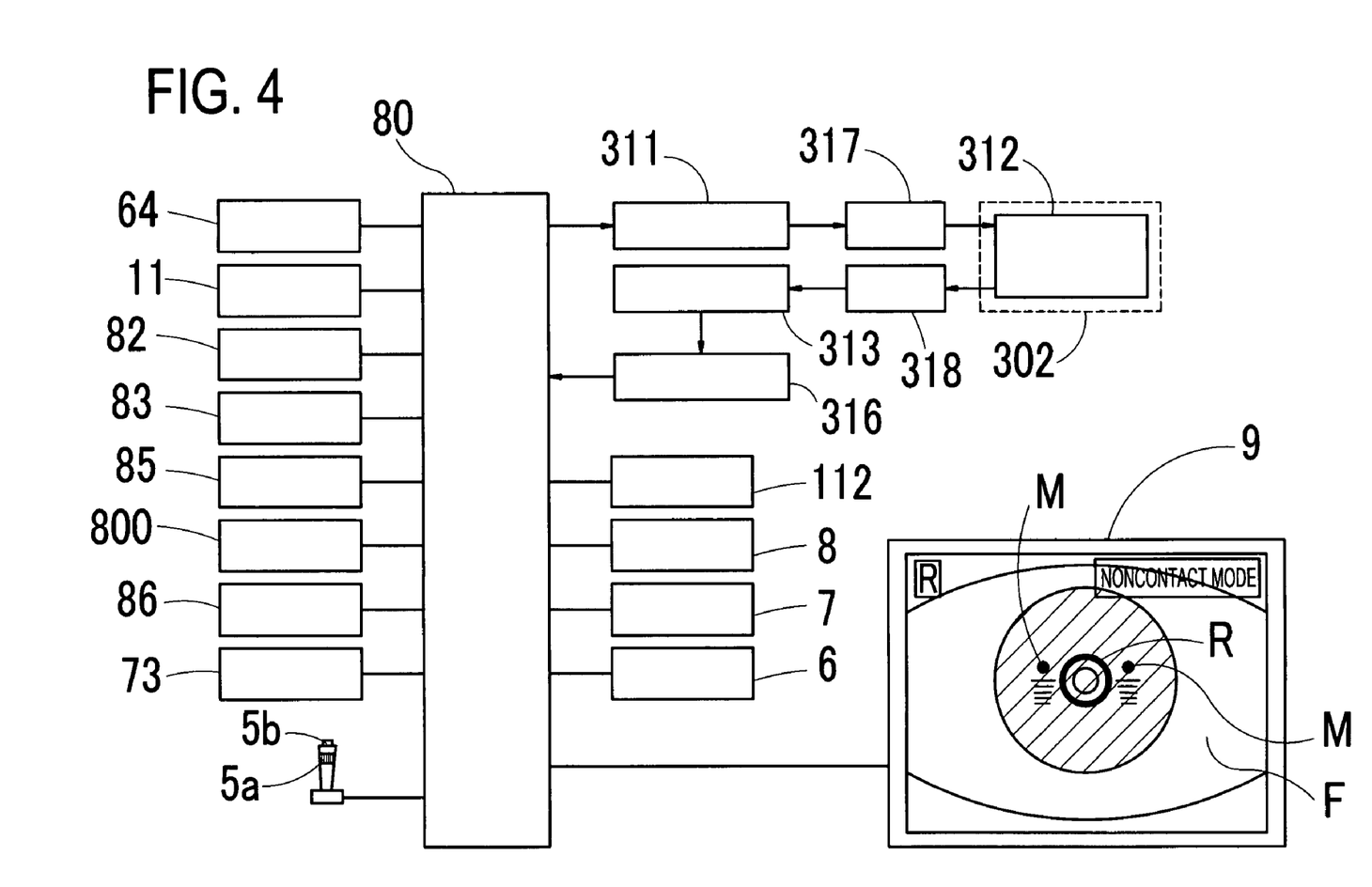
FIG. 4 is a view for explaining a control system of the eye axial length measurement apparatus of the embodiment.

A description will be given to optical systems of the eye axial length measurement apparatus of the present embodiment, the configuration of the contact measurement section 4b, and the configuration of the control system of the present apparatus. FIGS. 2A and 2B and FIG. 3 are views for explaining the configuration of an optical system of the non-contact measurement section 4a. FIG. 4 is a view for explaining the configuration of a control system of the eye axial length measurement apparatus. The optical systems includes a fundus irradiation optical system 100a, a cornea irradiation optical system 200a, a fundus photo-receiving optical system 100b, a cornea photo-receiving optical system 200b, a reference light optical system 500, a spectral optical system 600 (see FIG. 3), and an observation optical system 700.

The fundus irradiation optical system 100a and the cornea irradiation optical system 200a share a light source 11 which emits low coherent light. Part of light emitted from the light source 11 is focused on the cornea and the fundus of the patient's eye respectively to serve as first measuring light (cornea measuring light) and second measuring light (fundus measuring light). The optical systems of the present embodiment include a splitting means (e.g. a half mirror 20) for splitting reference light from the part of light emitted from the light source 11 and an optical path length changing means (e.g. a triangular prism 23 and a driving section 82) for changing the optical path length of the reference light. Thus, the optical path length of the reference light is changed by the optical path length changing means. Simultaneously, the reference light is synthesized with reflection light of the first measuring light and reflection light of the second measuring light respectively and made to interfere with each reflection light. The resultant interference lights are photo-received.

As shown in FIG. 2A, the part of light emitted from the light source 11 is irradiated to the fundus of the patient's eye E via a collimator lens 12, a half mirror 13, a condenser lens 14, a triangular prism 15, the half mirror 13, a relay lens 18, a relay lens 19, a half mirror 20, a dichroic mirror 21, and an objective lens 22. Specifically, those optical members arranged on an optical path between the collimator lens 12 and the objective lens 22 inclusive constitute the fundus irradiation optical system 100a. Reflection light from the fundus of the patient's eye E travels back along the optical path of the fundus irradiation optical system 100a, from the objective lens 22 to the condenser lens 14, in a reverse direction to the forward traveling direction of the fundus measuring light to be irradiated to the fundus. This reflection light then enters an end 25a of an optical fiber 25 via the half mirror 13 and a condenser lens 24. Specifically, the optical members arranged on an optical path between the objective lens 22 and the end 25a of the optical fiber 25 inclusive constitute the fundus photo-receiving optical system 100b.

As shown in FIG. 2B, the part of the light emitted from the light source 11 is irradiated to the vicinity of the cornea of the patient's eye E via the collimator lens 12, the half mirror 13, a movable triangular prism 23, the half mirror 13, the relay lens 18, the relay lens 19, the half mirror 20, the dichroic mirror 21, and the objective lens 22. Specifically, the optical members arranged on an optical path between the collimator lens 12 and the objective lens 22 inclusive constitute the cornea irradiation optical system 200a. Reflection light from the cornea of the patient's eye E travels back along the optical path of the cornea irradiation optical system 200a, from the objective lens 12 to the movable triangular prism 23, in a reverse direction to the forward traveling direction of the cornea measuring light to be irradiated to the cornea. This reflection light is then reflected by the half mirror 13 and converged by the condenser lens 24 to enter the end 25a of the optical fiber 25. Specifically, the optical members arranged on an optical path between the objective lens 22 and the end 25a of the optical fiber 25 inclusive constitute the cornea photo-receiving optical system 200b.

The reference light optical system 500 for generating reference light to be synthesized with the aforementioned fundus measuring light or cornea measuring light includes, in the order from the light source side, the light source 11, the collimator lens 12, the movable triangular prism 23, the half mirror 13, the relay lens 18, the relay lens 19, a reflection mirror 51, a reflection mirror 52, a relay lens 53, and a reference mirror 54. The movable triangular prism 23 movable in an arrow A direction is driven by the driving section 82 to change the optical path length of the reference light. According to the optical arrangement in the present embodiment, the optical path length of the cornea measuring light and the optical path length of the reference light are changed simultaneously in association with movement of the triangular prism 23. The low coherent light emitted from the light source 11 travels along the same path as that of the cornea irradiation optical system 200a until the light is allowed to pass through the half mirror 20. The light having passed through the half mirror 20 reaches the reference mirror 54 via the mirror 51, the mirror 52, and the relay lens 53. The light falling on the reference mirror 54 is turned back, passes through the relay lens 53, is reflected by the mirrors 52 and 51, and passes through the half mirror 20. This light having passed through the half mirror 20 is synthesized with the cornea reflection light into the interference light. This interference light travels along the same path as that of the cornea photo-receiving optical system 200b and enters the end 25a of the optical fiber 25. In this case, irrespective of the position of the movable triangular prism 23, the total optical path length of the cornea measuring light (from the light source 11 to the cornea and from the cornea to the end 25a of the optical fiber 25) and the total optical path length of the reference light (from the light source 11 to the reference mirror 54 and from the reference mirror 54 to the end 25a of the optical fiber 25) are maintained to be nearly equal in such a range that the cornea measuring light and the reference light can interfere with each other.

Further, when the optical path length of the reference light is changed by changing the position of the prism 23, the total optical path length of the reference light generated by the reference light optical system 500 and the total optical path length (from the light source 11 to the fundus and from the fundus to the end 25a of the optical fiber 25) of the fundus measuring light, which varies according to the axial length of a patient's eye, sometimes become nearly equal in such a range that the fundus measuring light and the reference light can interfere with each other. In this case, the light falling on the reference mirror 54 is turned back by the movable triangular prism 23 and is reflected by the half mirror 13 while the light is synthesized with the fundus reflection light turned back by the triangular prism 15 to produce the interference light, which then enters the end 25a of the optical fiber 25.

FIG. 3 is a schematic configuration view of a spectral optical system of the non-contact measurement section 4a of the present embodiment. The spectral optical system 600 (a spectrometer section) includes a collimator lens 60, a grating mirror (diffraction grid) 61, a condenser lens 62, a cylindrical lens 63, and a photo-receiving element (photodetector) 64. The photo-receiving element 64 used in the present embodiment is a one-dimensional device (a line sensor) having sensitivity to an infrared region.

The interference light produced by the cornea measuring light entering the end 25a of the optical fiber 25 and the reference light and the interference light generated by the fundus measuring light and the reference light are emitted from the other end 25b of the optical fiber 25. Two interference lights emerging from the end 25b are expanded in diameter by the collimator lens 60 and dispersed into frequency components by the grating mirror 61. The frequency-dispersed interference lights pass through the condenser lens 62 and the cylindrical lens 63 to converge on a photo-receiving surface of the photo-receiving element 64.

Returning to FIGS. 2A and 2B, the observation optical system 700 includes, in the order from the front side of the patient's eye, the objective lens 22, the dichroic mirror 21, a relay lens 71, an imaging lens 72, and an imaging (image pickup) device 73 having sensitivity to an infrared region. It should be noted that a pupil of the patient's eye E and the imaging device 73 have a nearly conjugate positional relationship. The dichroic mirror 21 reflects most of the light from the light source 11 while transmitting part thereof, and also transmits the light for observation of an anterior segment of the eye E.

In front of the anterior segment of the patient's eye E, ring target projecting optical systems 45 and working distance target projecting optical systems 46 are placed in a symmetric relation to each other with respect to the observation optical axis. Each of the optical systems 45 emits near infrared light to project a ring target onto a cornea Ec of the patient's eye E. Each of the optical systems 46 emits near infrared light to detect an alignment state of the apparatus relative to the patient's eye E in a direction of a working distance by projecting an infinite target onto the cornea Ec of the patient's eye E. The ring target projecting optical system 45 is also used as an anterior segment illumination system for illuminating the anterior segment of the eye E. Further, the ring target can also be utilized as a target for measuring the shape of the cornea.

The configuration of the contact measurement section 4b is explained below referring to FIG. 4. Data on intensity of an echo signal obtained by the ultrasonic probe 302 for a mode A including a transducer 312 is first detected as an ultrasonic signal. Here, a controller 80 controls to drive a clock generating circuit 311 to generate (transmit) ultrasonic waves from the transducer 312 provided in the probe 302 via a transmitter 317. Reflection echo (wave) from each tissue of the patient's eye is received by the transducer 312 and converted into a digital signal by an A/D converter 313 via an amplifier 318. The reflection echo information converted into a digital signal is stored temporarily in a sampling member 316. The controller 80 creates measurement data based on the echo information stored in the sampling memory 316 and displays the created data on the display monitor 9.

The configuration of the control system is described below. The controller 80 controls the entire apparatus, calculates measurement values, and performs other operations and is connected to the display monitor 9, the Y driving section 6, the XZ driving section 7, the driving section 8, the memory 85 that stores measurement results and others, the rotary knob 5a, the measurement start button 5b, a measurement mode selector switch 112, and others, as well as each member of the non-contact measurement section 4a and the contact measurement section 4b. The controller 80 is arranged to determine appropriateness of obtained measurement results to switch between the measurement modes according to the state of the patient's eye or inform an examiner of the necessity of switching between the measurement modes.

The operation of the eye axial length measurement apparatus having the above configurations will be explained below. In this apparatus, the power-on initial setting is set to the non-contact measurement mode. In this case, the controller 80 initializes in advance the height of the measurement unit 4 to a predetermined height in order to make a smooth start of eye axial length measurement in non-contact manner. The controller 80 drives the Y driving section 6 to bring the measurement optical axis La of the non-contact measurement section 4a to almost the same height of the patient's eye E. The controller 80 further moves the contact measurement section 4b back away from the patient's eye E. Thus, the eye axial length measurement using the non-contact measurement section 4a becomes enabled (see FIG. 1A).

Here, alignment of the measurement unit 4 in the X-Y-Z directions relative to the patient's eye E is conducted. In the present embodiment, a right eye is first measured. The examiner manipulates the joystick 5 and the rotary knob 5a while observing the monitor 9 to make rough alignment so that an anterior segment image F imaged by the two-dimensional imaging device 73 appears on the monitor 9 (see FIG. 4). When a ring target R generated by the ring target projection optical system 45 and infinite target images M generated by the working distance projecting optical system 46 become imaged by the imaging device 73, the controller 80 controls to drive the Y driving section 6 and the XZ driving section 7 to move the measurement unit 4 in each of the X-Y-Z directions based on the alignment state of the measurement unit 4 with respect to the patient's eye detected by a predetermined manner. Thus, fine alignment of the measurement unit 4 with respect to the patient's eye E is conducted. In this case, the controller 80 calculates the coordinate of the center point of the ring target R detected by the imaging device 73 to determine the alignment state in the up/down and right/left directions relative to the patient's eye. Further, in the case where the measurement unit 4 is misaligned with the patient's eye E in the Z (working distance) direction, an interval between the infinite targets M formed on the cornea Ec by the working distance target projecting optical system 46 remains almost unchanged, whereas an image spacing of the aforementioned ring target R changes in a predetermined meridian direction. Utilizing this property, the controller 80 determines the alignment state in the working distance direction with respect to the patient's eye (the details are referred to U.S. Pat. No. 5,463,430 (JP 6(1994)-46999A)).

After completion of alignment, measurement is automatically started. In the case where an auto shot function is off, on the other hand, measurement is started when the examiner presses the measurement start button 5b after completion of alignment.

When the controller 80 causes the light source 11 to emit low coherent light, based on a signal for starting measurement, spectral information on interference fringes is recorded on the photo-receiving element 64. The spectral information is input to the controller 80 and analyzed by Fourier transform. Accordingly, information on eye characteristics of the patient's eye in the depth direction can be measured.

In the case of determining the axial length of the patient's eye E, the controller 80 drives the driving section 82 to sequentially move the movable prism 23, thereby determining the axial length of the patient's eye E based on the interference signal obtained from the spectral information received by the photo-receiving element 64 and the optical path length of the reference light (a result of operation of the optical path length changing means) that changes as the prism 23 is moved.

The controller 80 drives the driving section 82 to move the movable prism 23 in the arrow A direction from a reference position (in the present embodiment, a position where the optical path of the cornea irradiation optical system becomes shortest) indicated by a solid line, thereby sequentially changing the optical path length of the optical system through which the cornea measuring light and the reference light pass.

Figure 5:
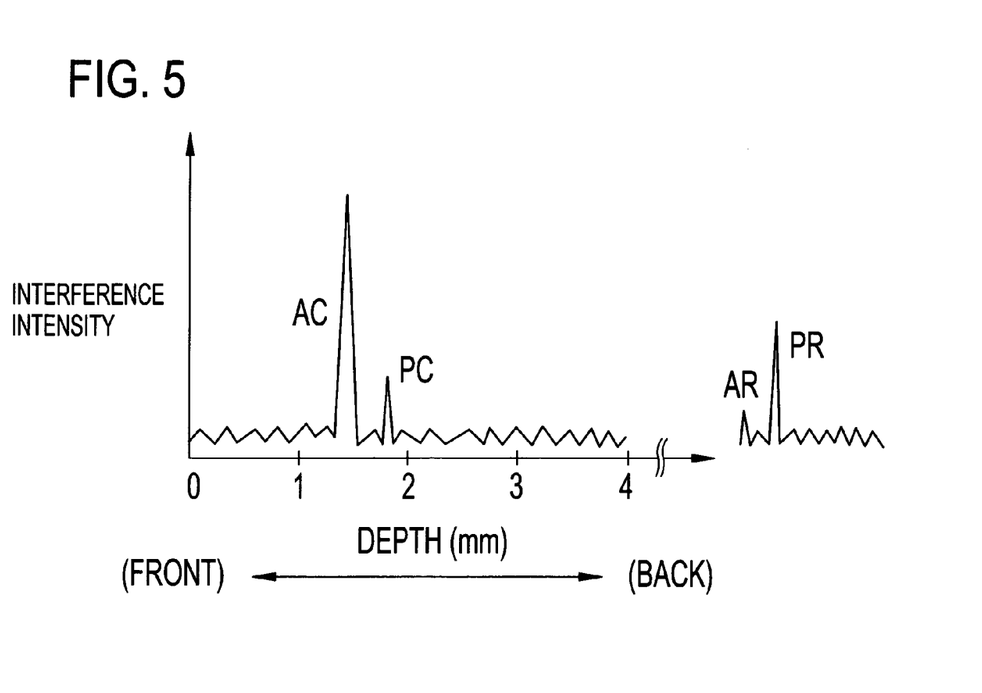
FIG. 5 is a graph showing interference signal intensity (interference intensity) in a depth direction of a patient's eye when only an interference signal generated by cornea measuring light and reference light is detected.

FIG. 5 is a graph showing an example of intensity of the interference signal (interference intensity) in a depth direction of the patient's eye when only the interference signal generated by the cornea measuring light and the reference light is detected. It is obtained based on the spectral information detected when the prism 23 is in the reference position. An interference signal AC is a signal of light reflected by an anterior surface of a cornea. An interference signal PC is a signal of light reflected by a posterior surface of the cornea. That is, the interference light generated by the cornea measuring light and the reference light includes the reflection lights by the corneal anterior and posterior surfaces. Accordingly, the corresponding interference signals are detected.

On the other hand, the interference signal generated by the fundus measuring light and the reference light is not detected at this stage. AR denotes an interference signal of light reflected by an anterior surface of a retina of the patient's eye and PR denotes an interference signal of light reflected by a posterior surface of the retina of the patient's eye. However, those signals are out of a measurement range at this stage.

Figure 6:
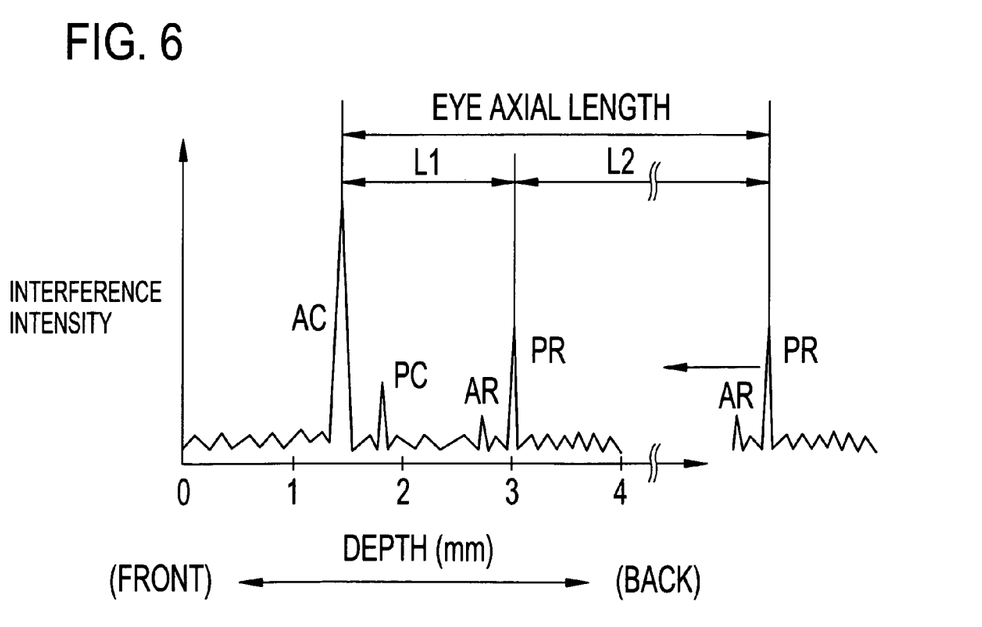
FIG. 6 is a graph showing interference signal intensity in the depth direction of the patient's eye when the interference signal generated by the cornea measuring light and the reference light and another interference signal generated by fundus measuring light and the reference light are detected.

When the optical path length of the reference light is increased as the movable triangular prism 23 is moved in the arrow direction, thus decreasing a difference in optical path length between the fundus measuring light and the reference light, interference light is generated by the fundus measuring light and the reference light. FIG. 6 is a graph showing an example of the intensity of the interference signal in the depth direction of the patient's eye when the interference signal generated by the cornea measuring light and the reference light and the interference signal generated by the fundus measuring light and the reference light are detected. In other words, the interference light of the fundus measuring light and the reference light includes the reflection lights from the anterior and posterior surfaces of the retina, so that the corresponding interference signals are detected.

The position of the prism 23 determined when both the interference signal AC and the interference signal PR are detected is different according to the axial length of a patients' eye. The controller 80 therefore specifies spectral information S representing that the interference signal AC and the interference signal PR are detected, from among plural pieces of spectral information stored in the memory 85 every time the position of the prism 23 is changed. Then, the controller 80 determines the positional information of the prism 23 (for example, a moving distance of the prism 23 from the reference position (or a driving amount of the driving section 82)) detected when the specified spectral information S is obtained. The controller 80 further determines the positional information of the interference signal AC and the interference signal PR in the depth direction based on the spectral information S obtained when the interference signal AC and the interference signal PR are detected.

The controller 80 performs an arithmetic operation on the axial length of the patient's eye based on the positional information of the prism 23 corresponding to the spectral information when the interference signal AC and the interference signal PR are detected and the positional information of the interference signal AC and the interference signal PR in the depth direction. In this case, the controller 80 calculates a rough eye axial length value from the positional information of the prism 23 and determines a fine eye axial length value from the positional information of the interference signal AC and the interference signal PR in the depth direction.

For instance, the controller 80 determines a dimension L1 in the depth direction between the interference signal AC and the interference signal PR based on the spectral information S representing that the interference signal AC and the interference signal PR are detected. The controller 80 further determines a dimension L2 based on the moving distance of the prism 23 from the reference position, at which the spectral information S is obtained. The controller 80 calculates the axial length of the patient's eye by adding the dimension L2 to the dimension L1 (the axial length is calculated by addition of L1 and L2). Then, the controller 80 stores the obtained information (measurement result) of the axial length of the patient's eye in the memory 85 and displays it on the monitor 9.

As to the axial length optical measurement to be executed as above, if the patient's eye is a sever cataract eye, the measuring light is likely to be blocked (scattered) by a cloudy portion of the eye, and scattered light will be incident on the photo-receiving element 64. This decreases measurement accuracy. In such a case, the non-contact measurement section 4a could not provide a highly reliable measurement result. Thus, the use of the contact measurement section 4b is more preferable for such measurement.

In the present embodiment, therefore, the controller 80 determines whether or not a measurement result of the right eye satisfies a predetermined measurement condition. If it is determined that the measurement result does not satisfy the measurement condition, it is stored in the memory 85 that the right eye of the patient is an eye for which the ultrasonic measurement is preferred to measure its axial length (the measurement result is judged as not satisfying the measurement condition).

Figure 7:
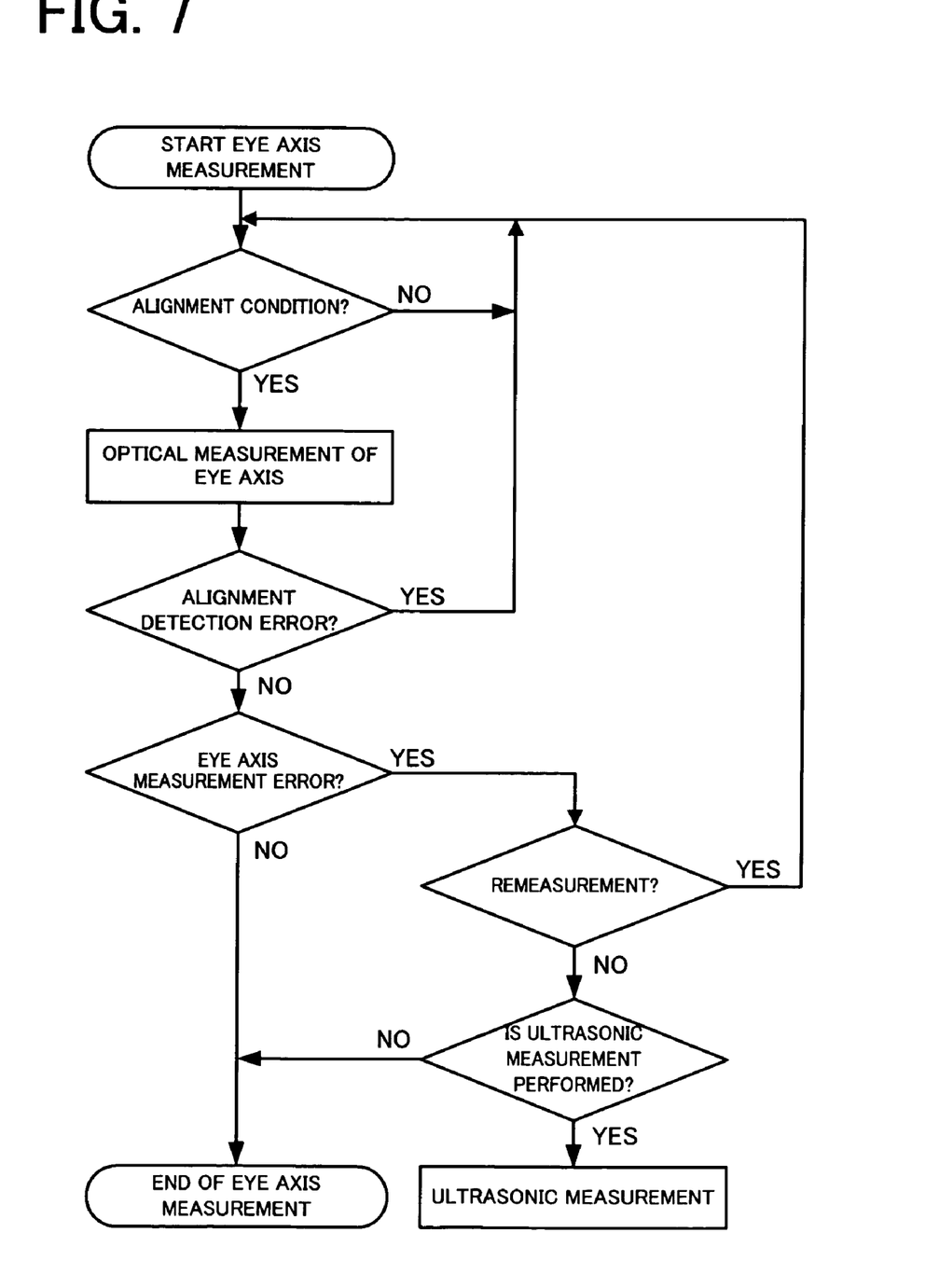
FIG. 7 is a flowchart showing an example of an operation of determining a measurement condition in the embodiment.

One of the determination manners will be described below referring to a flowchart of FIG. 7. Upon completion of alignment with respect to the right eye, the controller 80 checks in a first step the alignment state of the non-contact measurement section 4a with respect to the patient's eye for execution of measurement. Here, the controller 80 determines whether or not the degree of misalignment of the measurement unit 4 with respect to the patient's eye for execution of measurement is within a predetermined permissible range (e.g. whether or not the degree of misalignment from the alignment reference position in the X-Y-Z directions is 0.5 mm or less). The alignment check for execution of measurement can also be done not only based on an alignment target image detected by the imaging device 73 when the measuring light is received by the photo-receiving element 64 but also based on alignment target images detected by the imaging device 73 before and after the execution of measurement respectively.

Figure 8:
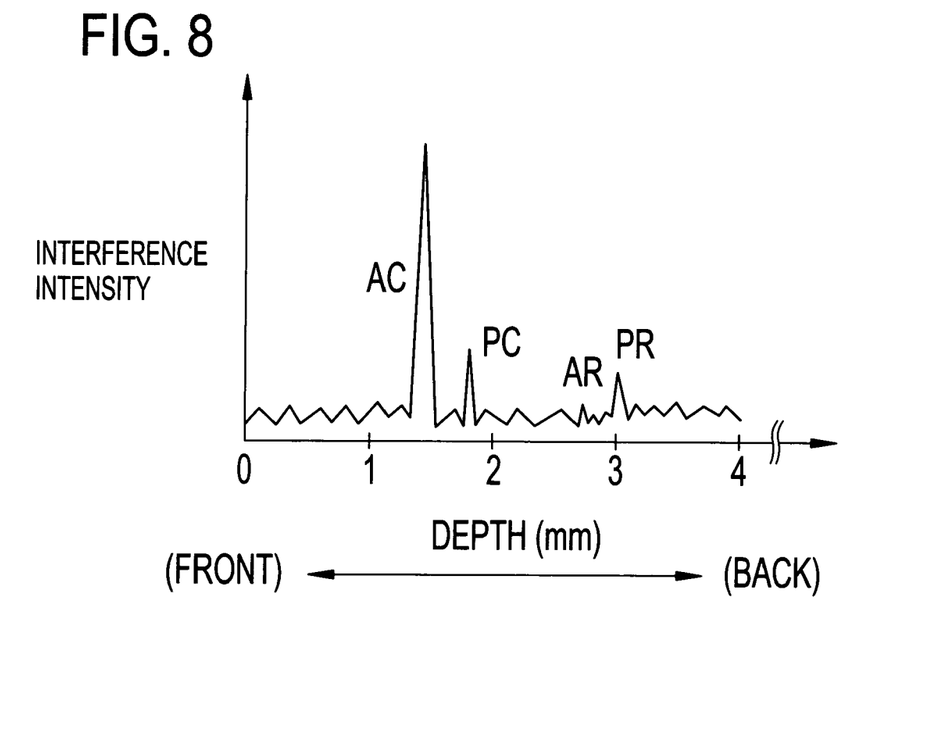
FIG. 8 is a graph showing an example of an interference signal of a cataract eye.

If it is determined that an alignment error is present, the controller 80 returns the non-contact measurement section 4a to a state that enables axial length measurement again. If it is determined that no alignment error is present, the controller 80 optically measures the axial length and then determines again as to the appropriateness of alignment. If this determination shows that an alignment error is present, the controller 80 returns the non-contact measurement section 4a to a state that enables axial length measurement again. If the determination shows that no alignment error is present, on the other hand, the controller 80 determines in a second step as to whether or not the interference signal generated by the fundus reflection light as above is appropriate. In the case of a cataract eye, the interference signals AC and PC generated by the reflection light from the cornea have peak values at a normal level as shown in FIG. 8. However, the interference signals AR and PR generated by the reflection light from the fundus have peak values at a lower level, so that the interference signals entirely include noise light resulting from scattered light. In the second step, therefore, the controller 80 determines whether or not the peak values of the interference signals AR and PR meet a predetermined value. In this case, the level of backgrounds of the entire interference signals or full-width of half-maximum of the interference signal AR, the interference signal PR, or others may be used. It should be noted that the above step can be utilized as one measure for checking whether or not a transparent body of the patient's eye has an unacceptable cloudy portion.

If it is determined in the second step that no eye axial length measurement error is found, the measurement is terminated. If it is determined an eye axial length measurement error is found, on the other hand, the controller 80 displays an indication to urge the examiner to decide whether or not the measurement is to be performed again (for example, a message on the monitor 9 to ask the examiner whether or not remeasurement is to be conducted). Upon receipt of a signal representing transition to remeasurement from a predetermined switch on a control section 86, the controller 80 returns the non-contact measurement section 4a to the state that enables the eye axial length measurement again. The remeasurement step is provided to give an opportunity of remeasurement by the non-contact measurement section 4a in consideration of a burden on the patient's eye and an additional work for the examiner in the ultrasonic measurement.

Upon receipt of a signal entered by the examiner by a predetermined switch operation indicating that remeasurement is not to be conducted, the controller 80 stores in the memory 85 that the patient's right eye is an eye for which the ultrasonic measurement is preferred to measure its axial length (i.e. an eye that does not meet the predetermined measurement condition). After completion of measurement of the right eye as above, the examiner manipulates the joystick 5 to move the non-contact measurement section 4a to the front of the left eye and similarly makes alignment of the measurement section 4a with the left eye to measure the axial length of the left eye. After the determination similar to that for the right eye, upon receipt of the signal representing that remeasurement is not to be conducted, the controller 80 stores in the memory 85 that the patient's left eye is an eye for which the ultrasonic measurement is preferred to measure its axial length.

If it is determined (it is stored in the memory 85) that at least one of the right and left eyes is an eye for which the ultrasonic axial length measurement is preferred (an eye that does not meet the predetermined measurement condition), the controller 80 controls to switch to the contact measurement mode so as to measure the axial length of the patient's eye by use of the contact measurement section 4b or indicates to that effect (for instance, the controller 80 displays a message on the monitor 9 to urge switching of the measurement mode). The controller 80 also displays an indication on the monitor 9 to indicate which patient's eye, right or left, is an eye for which the ultrasonic axial length measurement is preferred. In other words, the controller 80 determines whether or not a measurement result satisfies the predetermined measurement condition. If it is determined that at least one of the right eye and the left eye does not satisfy the measurement condition, the controller 80 indicates that the axial length measurement is to be conducted in the contact measurement mode or automatically switches to the contact measurement mode.

When the mode selector switch 112 is pressed by the examiner based on the above indication, the controller 80 generates a signal representing the switching to the contact measurement mode to change the measurement screen of the monitor 9 and the apparatus configuration to corresponding ones. Alternatively, the controller 80 automatically generates the signal representing the switching to the contact measurement mode to change the measurement mode to the contact measurement mode. If it is determined that the ultrasonic measurement is not to be conducted, the measurement is terminated.

As described above, when it is determined that the alignment state is appropriate for execution of measurement of at least one of the right eye and the left eye and additionally that the interference signal generated by the fundus reflection light is error, the controller 80 judges that any accurate measurement result is not obtained in the non-contact measurement mode and a more accurate measurement result is obtainable in the contact measurement mode. The controller 80 controls to switch to the contact measurement mode so as to measure the axial length of the patient's eye by use of the contact measurement section 4b or indicates to that effect. Accordingly, in the case where there is a high possibility that the transparent body of the patient's eye has a cloudy portion unacceptable (unmeasurable) in the non-contact measurement mode, the switching to the contact measurement mode is conducted. Further, in the case where it is determined that the error is caused by another reason such as misalignment and thus the measurement in the non-contact measurement mode is practicable, the measurement using the non-contact measurement section 4a is performed again. The appropriateness of alignment is taken into consideration as above because the interference signal will fluctuate even by the effect of misalignment and it is hard to specify the cause of a decrease in reliability from only a determination result on the appropriateness of the interference signal. It also may be arranged such that, when the measurement is performed again by the non-contact measurement section 4a and a determination result shows an alignment error again, the measurement mode is switched to the contact measurement mode. The above description includes the step of determining whether or not the remeasurement is to be performed after the determination, but this step may be omitted. Another alternative is to determine whether or not the right eye and the left eye satisfy a predetermined measurement condition respectively after measurements of the right and left eyes and to specify the eye for which the ultrasonic axial length measurement is preferred (a remeasurement step may be provided). In the above explanation, the measurement condition is checked after measurement, but may be checked during measurement.

An explanation is given to the operation after the signal representing the switching to the contact measurement mode is generated. The examiner applies eye-drops for anesthesia to the patient's eye to be measured by the contact measurement section 4b. When the mode switching signal is generated, the controller 80 drives the Y driving section 6 to move the measurement unit 4 downward so that the measurement axis Lb of the contact measurement section 4b comes to almost the same height as the patient's eye E (see FIG. 1B). In this case, moving the measurement unit 4 is preferably performed under the condition that the sliding mechanism not shown for moving the movable base 3 relative to the table 1 is provided with a brake mechanism (a lock mechanism) against the movement of the movable base 3 in the back/forth direction and the movable base 3 is held against backward/forward movement with respect to the table 1. The brake mechanism may be automatically activated in the contact measurement mode, thereby eliminating the need for additional work by the examiner.

The controller 80 guides an alignment manipulation by the examiner or an alignment operation of the apparatus for making the ultrasonic measurement of the axial length of the patient's eye determined to be an eye for which the ultrasonic axial length measurement is preferred (an eye determined that it does not satisfy the measurement condition in the non-contact measurement mode). If the examiner makes alignment, for instance, an indication is displayed on the monitor 9 to guide the examiner to move the movable base 3 toward the patient's eye (hereinafter, referred to as a "measurement eye") for which the ultrasonic axial length measurement is preferred so that the contact measurement section 4b is moved to the front of the measurement eye (e.g. a right-pointing arrow is displayed if the left eye is the measurement eye). If the apparatus operation is to be guided, for instance, a movable range of the XZ driving section 7 in the right/left direction may be set to be larger (e.g. to about an interpupillary distance) so that the contact measurement section 4b is automatically moved by driving of the XZ driving section 7 to the front of the measurement eye. It is to be noted that if both eyes do not satisfy the measurement condition, the alignment is guided to either one of the eyes.

When the contact measurement section 4b is placed in front of the measurement eye in the above manner, the controller 80 moves the contact measurement section 4b toward the patient's eye E automatically or in response to an operation signal from a predetermined forward/backward movement switch provided on the control section 86, thereby bringing the distal end of the ultrasonic probe 302 close to the patient's eye E. In this case, it is preferable that the probe 302 is mounted in a housing of the contact measurement section 4b by use of an elastic member such as a spring so that the distal end of the probe 302 does not strongly touch or abut on the eye. Further, in the case of automatic movement, a forward movement distance of the probe 302 is determined to be a working distance (a distance from the forefront surface of the measurement section 4a to the corneal apex of the patient's eye) of the measurement unit 4 with respect to the patient's eye in the non-contact measurement mode, and the probe 302 is arranged to slowly move (protrude) forward from the forefront surface of the measurement section 4a. The probe 302 can be moved further forward by a manual operation if the forward movement distance is insufficient.

After the forward movement is performed as above and when an echo signal from the patient's eye is detected appropriately, the controller 80 causes the driving section 8 to stop the forward movement of the ultrasonic probe and starts the axial length measurement. In this case, when a plurality of measurement values of the axial length becomes steady and a prescribed number of measurement values is obtained, the measurement is automatically terminated. The controller 80 then drives the driving section 8 to move the contact measurement section 4b away from the patient's eye E, thus moving the ultrasonic probe 302 backward. Alternatively, this backward movement operation may be performed manually by the examiner. Upon completion of the measurement as above, the lock state of the movable base 3 against the table 1 is released and simultaneously the driving mechanism is driven to move the movable base 3 to an initial position so that the non-contact measurement section 4a comes to the same height as the patient's eye.

The above ultrasonic axial length measurement can provide a high reliable measurement result without any particular influence from a cataract eye. According to the above configuration, specifically, a high reliable measurement result can be obtained efficiently. By the switching to the contact measurement mode is guided by an indication or is automatically performed based on the result of determination on the reliability of the measurement result, as mentioned above, the measurement can be performed appropriately even by an inexperienced examiner.

Figure 9:
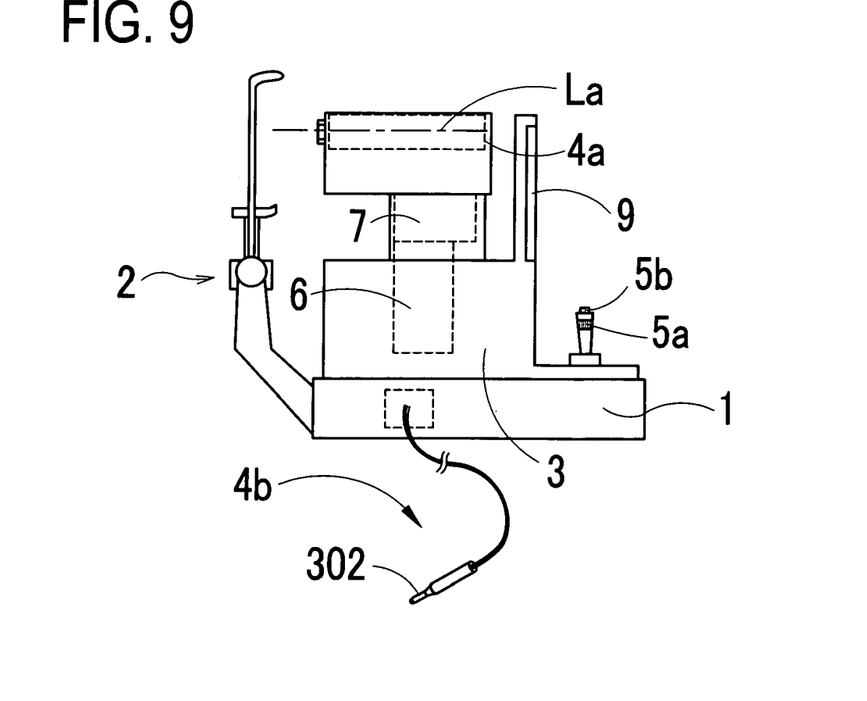
FIG. 9 is an external view of a modified example of the present invention.

In the above description, the non-contact measurement section 4a and the contact measurement section 4b are integrally combined and mounted on the movable base 3. However, the present invention can be applied to another arrangement that the ultrasonic probe 302 is designed to be held by an examiner and connected to an apparatus main unit containing the non-contact measurement section 4a through a cable or the like (see FIG. 9).

The determination step to be used in the non-contact measurement mode as one measure for checking whether or not the transparent body of the patient's eye has an unacceptable cloudy portion is not limited to the above manner. Alternatively, for example, it may be arranged such that the reflection light irradiated to the fundus by the fundus irradiation optical system 100a is delivered to the observation optical system 700 in which a diaphanoscopy image of the patient's eye is imaged by the imaging device 73 so that whether or not the patient's eye has an unacceptable cloudy portion is determined based on a result of the imaged image. To be concrete, it is conceivable to determine whether or not distribution of the cloudy portion in the imaged diaphanoscopy image (a portion with a low photo-receiving level in a pupil image) has a predetermined area or larger. It also may be determined whether or not a region through which the measuring light passes (e.g. a region within 1 mm or less in radius around the measurement optical axis La) has a cloudy portion (determination of a blocked state of the measuring light).

Further, it may be arranged such that an anterior segment section imaging optical system capable of imaging a cross section of an anterior segment of a patient's eye (e.g. an imaging optical system arranged to optically section the anterior segment of the patient's eye by slit light to obtain a sectional image of the anterior segment by the imaging optical system disposed based on Scheimpflug's principle) is arranged in the non-contact measurement section 4a, and the obtained sectional image is analyzed by image processing to determine whether or not the patient's eye has a cloudy portion (see U.S. Pat. No. 6,805,442 (JP 2003-24280A) for example).

Furthermore, it may be arranged such that the axial length is measured plural times by the non-contact measurement section 4a and whether or not variations of measurement results of the plural measurements are in a permissible range. For instance, it is determined whether or not a difference between a minimum value and a maximum value of the plural measurement results exceeds an acceptable value.

The manner of determining whether or not the measurement result in the non-contact measurement mode satisfies the predetermined measurement condition can be achieved by various combinations and appropriate settings. For instance, it may be arranged such that a reliability coefficient (e.g. ten integers from 1 to 10) of a measurement result is calculated from the variations of the results of the plural measurements and it is determined whether or not the calculated reliability coefficient satisfies a predetermined value.

In the above description, the determination step includes determining whether or not alignment is appropriate in order to execute the remeasurement without switching to the contact measurement mode when the reliability of the measurement result is damaged due to misalignment. Instead of such determination of the appropriateness of misalignment, another determination step mentioned below may be adopted.

For instance, the controller 80 determines whether the measuring light is eclipsed by an iris. In this case, an iris part and a pupil part of the patient's eye are imaged by the observation optical system 700 and the contour of a pupil image is extracted by image processing. Whether or not the measuring light is eclipsed by the iris can be determined based on whether or not a transmission area of the measuring light is present in the extracted pupil contour part.

The controller 80 further determines whether or not the patient's eye blinks during measurement. If the patient's eye blinks during measurement, outputs of the photo-receiving element 64 will lower or fluctuate. Accordingly, this behavior may be utilized to determine the presence/absence of eye blinking. It is to be noted that various techniques have been disclosed to detect the presence of eye blinking of a patient and thus one of those techniques may be adopted to detect the eye blinking. For instance, it is possible to determine the presence of eye blinking by the imaging device 73 that detects the presence or absence of a corneal luminescent spot formed on the cornea of the patient's eye by a predetermined projecting optical system.

Further, in the case where it is determined that the measurement result in the non-contact measurement mode does not satisfy the aforementioned predetermined measurement condition, original data used in the determination such as a graph showing waveforms of the interference signal as shown in FIG. 8 and the diaphanoscopy image may be displayed on the monitor 9. This configuration allows the examiner to confirm whether or not the switching to the contact measurement mode is performed.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An eye axial length measurement apparatus comprising:
a light source which emits a low coherent light;
a non-contact eye axial length measurement unit for optically measuring an axial length of a patient's eye in a non-contact manner in such a way that the low coherent light emitted from the light source is split into a measuring light and a reference light, the measuring light and the reference light being caused to interfere with each other and received by a photo-receiving element, and the eye axial length being calculated based on a difference in optical path length between the measuring light and the reference light when an interference signal is generated;
an ultrasonic eye axial length measurement unit including an ultrasonic probe with a transducer, the ultrasonic eye axial length measurement unit being placed in a position with a deviation from the non-contact eye axial length measurement unit;

an XYZ driving unit including a base, a head support unit attached to the base, and a movable unit which supports the non-contact eye axial length measurement unit and the ultrasonic eye axial length measurement unit movably in X-Y-Z directions with respect to the base; and determination means which determines whether a cloudy portion which is an obstacle to measurement by the non-contact eye axial length measurement unit is present, based on one of a measurement result of the non-contact eye axial length measurement unit and an imaging result of an anterior segment section imaging unit placeable in the non-contact eye axial length measurement unit.

2. An eye axial length measurement apparatus comprising:

a light source which emits a low coherent light;

a non-contact eye axial length measurement unit for optically measuring an axial length of a patient's eye in a non-contact manner in such a way that the low coherent light emitted from the light source is split into a measuring light and a reference light, the measuring light and the reference light being caused to interfere with each other and received by a photo-receiving element, and the eye axial length being calculated based on a difference in optical path length between the measuring light and the reference light when an interference signal is generated;

an ultrasonic eye axial length measurement unit including an ultrasonic probe with a transducer, the ultrasonic eye axial length measurement unit being placed in a position with a deviation from the non-contact eye axial length measurement unit;

an XYZ driving unit including a base, a head support unit attached to the base, and a movable unit which supports the non-contact eye axial length measurement unit and the ultrasonic eye axial length measurement unit movably in X-Y-Z directions with respect to the base; and control means for driving the XYZ driving unit in a vertical direction and a horizontal direction, based on a signal representing a switch from a measurement mode using the non-contact eye axial length measurement unit to a measurement mode using the ultrasonic eye axial length measurement unit, so that a measurement central axis of the ultrasonic eye axial length measurement unit is adjusted to a position in which a measurement central axis of the non-contact eye axial length measurement unit has been positioned before the switch.

3. An eye axial length measurement apparatus comprising:

a first measurement unit, including a light source which emits a low coherent light, for optically measuring an axial length of a patient's eye in a non-contact manner in such a way that the low coherent light emitted from the light source is split into a measuring light and a reference light, the measuring light and the reference light being caused to interfere with each other and being received by a photo-receiving element, and the eye axial length being calculated based on a difference in optical path length between the measuring light and the reference light when an interference signal is generated;

a second measurement unit, including an ultrasonic probe with a transducer, for measuring the axial length of the patient's eye in a contact manner in such a way that an ultrasonic wave transmitted from the transducer is reflected by the patient's eye and received by the transducer, and the eye axial length is calculated based on reflection echo information, the second measurement unit being placed in a position with a deviation from the first measurement unit;

a moving unit including a base and a movable unit which supports the first and second measurement units movably in up and down, right and left, and back and forth directions with respect to the base; and a determination unit which determines whether a cloudy portion of the patient's eye which is an obstacle to measurement by the first measurement unit is present, based on one of a measurement result by the first measurement unit, an imaging result by an anterior segment imaging unit which images an image of an anterior segment of the patient's eye, and an imaging result by a fundus imaging unit which images an image of a fundus of the patient's eye, wherein the moving unit is adapted to move the movable unit so that a measurement central axis of the second measurement unit is aligned with a position in which a measurement central axis of the first measurement unit has been positioned.

4. The eye axial length measurement apparatus according to claim 3, wherein the determination unit determines whether the cloudy portion is present based on a peak value of the interference signal generated by the measuring light reflected by the patient's eye.

5. The eye axial length measurement apparatus according to claim 3, wherein the determination unit determines that a remeasurement by the second measurement unit is to be performed when it is determined that the cloudy portion is present, and indicates that the remeasurement should be performed.

6. The eye axial length measurement apparatus according to claim 3, wherein the determination unit determines whether the cloudy portion is present based on variations of a plurality of measurement results by the first measurement unit.

7. The eye axial length measurement apparatus according to claim 3, further comprising an alignment unit which detects an alignment state of the measurement central axis of the first measurement unit with the patient's eye, and the determination unit determines whether the cloudy portion is present when the measurement central axis of the first measurement unit is aligned with the patient's eye.

8. An eye axial length measurement apparatus comprising:

a first measurement unit, including a light source which emits a low coherent light, for optically measuring an axial length of a patient's eye in a non-contact manner in such a way that the low coherent light emitted from the light source is split into a measuring light and a reference light, the measuring light and the reference light being caused to interfere with each other and being received by a photo-receiving element, and the eye axial length being calculated based on a different in optical path length between the measuring light and the reference light when an interference signal is generated;

a second measurement unit, including an ultrasonic probe with a transducer, for measuring the axial length of the patient's eye in a contact manner in such a way that an ultrasonic wave transmitted from the transducer is reflected by the patient's eye and received by the transducer, and the eye axial length is calculated based on reflection echo information, the second measurement unit being placed in a position with a deviation from the first measurement unit;

a moving unit including a base and a movable unit which supports the first and second measurement units movably in up and down, right and left, and back and forth directions with respect to the base; and a control unit which controls to drive the moving unit, based on a signal representing a switch from a first measurement mode using the first measurement unit to a second measurement mode using the second measurement unit, so that a measurement central axis of the second measurement unit in the second measurement mode is aligned with a position in which a measurement central axis of the first measurement unit has been positioned in the first measurement mode.

9. The eye axial length measurement apparatus according to claim 8, further comprising a determination unit which determines whether a cloudy portion of the patient's eye which is an obstacle to measurement in the first measurement mode is present, based on one of a measurement result by the first measurement unit, an imaging result by an anterior segment imaging unit which images an image of an anterior segment of the patient's eye, and an imaging result by a fundus imaging unit which images an image of a fundus of the patient's eye.

10. The eye axial length measurement apparatus according to claim 9, wherein the determination unit determines whether the cloudy portion is present based on a peak value of the interference signal generated by the measuring light reflected by the patient's eye.

11. The eye axial length measurement apparatus according to claim 9, wherein the determination unit determines that a remeasurement in the second measurement mode is to be performed when it is determined that the cloudy portion is present, and generates the signal representing the switch from the first measurement mode to the second measurement mode.

12. The eye axial length measurement apparatus according to claim 9, wherein the determination unit determines whether the cloudy portion is present based on variations of a plurality of measurement results by the first measurement unit.

13. The eye axial length measurement apparatus according to claim 9, further comprising an alignment unit which detects an alignment state of the measurement central axis of the first measurement unit with the patient's eye, the determination unit determines whether the cloudy portion is present when the measurement central axis of the first measurement unit is aligned with the patient's eye.

14. An eye axial length measurement apparatus comprising:

a first measurement unit, including a light source which emits a low coherent light, for optically measuring an axial length of a patient's eye in such a way that the low coherent light emitted from the light source is split into a measuring light and a reference light, the measuring light and the reference light being caused to interfere with each other and received by a photo-receiving element, and the eye axial length being calculated based on a difference in optical path length between the measuring light and the reference light when an interference signal is generated;

a second measurement unit including an ultrasonic probe with a transducer, for measuring the axial length of the patient's eye in such a way that an ultrasonic wave transmitted from the transducer is reflected by the patient's eye and received by the transducer, and the eye axial length is calculated based on reflection echo information;

a moving unit including a base and a movable unit which supports the first measurement unit movably in up and down, right and left, and back and forth directions with respect to the base; and a monitor, which displays a measurement result by the first measurement unit and a measurement result by the second measurement unit.

15. The eye axial length measurement apparatus according to claim 14, further comprising a determination unit which determines whether a cloudy portion of the patient's eye which is an obstacle to measurement by the first measurement unit is present, based on one of a measurement result by the first measurement unit, an imaging result by an anterior segment imaging unit which images an image of an anterior segment of the patient's eye, and an imaging result by a fundus imaging unit which images an image of a fundus of the patient's eye.

16. The eye axial length measurement apparatus according to claim 15, wherein the determination unit determines that a remeasurement by the second measurement unit is to be performed when it is determined that the cloudy portion is present, and indicates that the remeasurement should be performed.

17. The eye axial length measurement apparatus according to claim 14, further comprising:

a mode switching unit which generates a signal representing a switch from a first measurement mode using the first measurement unit to a second measurement mode using the second measurement unit; and a control unit which controls the monitor to change a measurement screen of the monitor, based on the signal representing the switch from the first measurement mode to the second measurement mode by the mode switching unit.

* * * * *